(12) United States Patent
Montanari

(10) Patent No.: US 6,881,843 B2
(45) Date of Patent: Apr. 19, 2005

(54) PROCESS FOR PRODUCTION OF GABAPENTIN INTERMEDIATE

(75) Inventor: Stefania Maria Paola Montanari, Milan (IT)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 10/455,314

(22) Filed: Jun. 6, 2003

(65) Prior Publication Data

US 2003/0195358 A1 Oct. 16, 2003

Related U.S. Application Data

(62) Division of application No. 09/984,058, filed on Oct. 26, 2001, now Pat. No. 6,613,904.
(60) Provisional application No. 60/244,891, filed on Nov. 2, 2000.

(51) Int. Cl.⁷ .............................................. C07D 221/20
(52) U.S. Cl. ........................................ 546/183; 568/376
(58) Field of Search ........................... 546/183; 568/376

(56) References Cited

U.S. PATENT DOCUMENTS 4,024,175 A    5/1977  Satzinger et al.
5,091,567 A    2/1992  Geibel et al.

FOREIGN PATENT DOCUMENTS

WO    WO97/33858    9/1997

OTHER PUBLICATIONS

Holder, R. W. et al., "Geminate–Substituted Cyclopentadienes. 1. Synthesis of 5,5–Dialkylcyclopentadienes via 4,4–Dialkylcyclopent–2–en–l–ones", *J. Org. Chem.* 1982, vol. 47, pp. 1445–1451.

Thorpe et al.; paper entitled, The Formation and Reactions of Imino Compounds: Part XVIII. The Condensation of cycloHexanones with Cyanoacetamide Involving the Displacement of an Alkyl Group. J. Chem. Soc. 1913, pp. 1586–1600.

Vogel, A.I., paper entitled Physical Properties and Chemical Constitution: Part II. Esters of ββ–Substituted Glutaric Acids. J. Chem. Soc., 1934, pp. 1758–1765.

*Primary Examiner*—Kamal Saeed
(74) *Attorney, Agent, or Firm*—Kenyon & Kenyon

(57) ABSTRACT

The invention relates to a novel process for producing a the intermediary compound α,α',dicyano-β,β-pentamethyleneglutarimide. The process includes the steps of reacting a ketone such as cyclohexanone with ethylcyanoacetate in the presence of ammonium hydroxide.

10 Claims, No Drawings

PROCESS FOR PRODUCTION OF GABAPENTIN INTERMEDIATE

This application is a divisional application of U.S. application Ser. No. 09/984,058 filed Oct. 26, 2001 now U.S. Pat. No. 6,613,904, and claims the filing date priority of U.S. Provisional Application No. 60/244,891 filed Nov. 2, 2000.

FIELD OF THE INVENTION

The present invention relates to a compound that is used as an intermediate in the production of gabapentin, and a process for production thereof. More particularly, the present invention relates to α,α',dicyano-β,β-pentamethyleneglutarimide, and a process for manufacturing α,α',dicyano-β,β-pentamethyleneglutarimide.

BACKGROUND OF THE INVENTION

Gabapentin, 1-(aminomethyl)-1-cyclohexaneacetic acid, has the chemical structure of formula II:

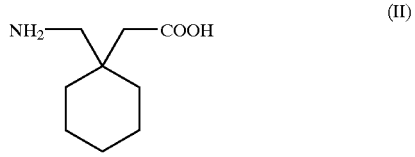

(II)

Gabapentin is used for treating cerebral diseases such as epilepsy, faintness attacks, hypokinesis and cranial traumas. U.S. Pat. No. 4,024,175 to Satzinger et al., incorporated herein by reference, discloses that gabapentin of formula (II) shows hypothermal and, in some cases, narcosis-potentiating or sedating properties as well as protective effect against cardiozole cramp in animals. Gabapentin is the active ingredient in Neurontin, marketed by Warner Lambert, and approved by the Food and Drug Administration as an anti-epileptic, anti-seizure, or anti-convulsant medication. As such, there has been a need for producing pure and stable gabapentin.

In one process for the preparation of gabapentin, an intermediary, α,α',dicyano-β,β-pentamethyleneglutarimide (formula I)

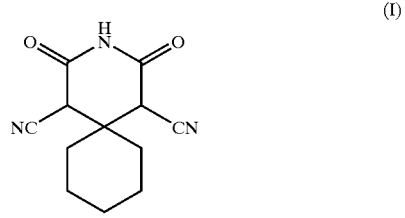

(I)

is produced by the Guareschi reaction in the following manner. Cyclohexanone and ethylcyanoacetate are reacted in an anhydrous environment in the presence of gaseous ammonia dissolved in ethanol. The reaction is represented as

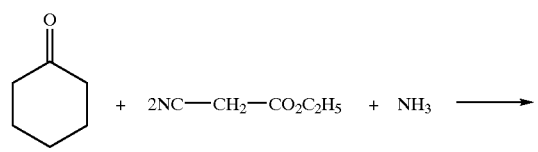

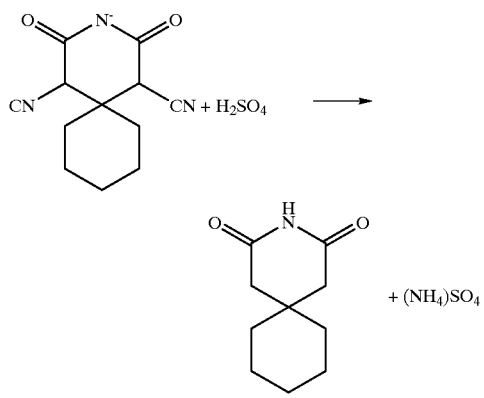

The Guareschi reaction is inefficient as the reaction requires at least 48 hours to proceed to completion, and more typically between 48–168 hours for completion. In addition, current environmental regulations make it impractical to produce gaseous $NH_3$ in ethanol on a large scale.

SUMMARY OF THE INVENTION

The present invention relates to a process for producing α,α',dicyano-β,β-pentamethyleneglutarimide (formula I) by reacting cyclohexanone and ethylcyanoacetate in the presence of ammonium hydroxide. The process of the present invention can be substantially completed in less than 24 hours. The reaction of the present invention can be processed in an aqueous environment and may include at least one solvent. The solvent can be methanol, ethanol or any similar solvent not having adverse affect on the reaction. Most importantly, a reaction of the present invention need not be conducted in an anhydrous environment.

DETAILED DESCRIPTION

We have discovered that contrary to previous practice in the art, the Guareschi reaction may be performed in the presence of water. Consequently, gaseous $NH_3$ can be replaced in the reaction of α,α',dicyano-β,β-pentamethyleneglutarimide by, for example, an aqueous solution of ammonium hydroxide. Such aqueous solutions are significantly easier to handle since they avoid many of the environmental concerns that would arise from handling gaseous $NH_3$ in ethanol.

Accordingly, in one embodiment of the invention a ketone is condensed with ethylcyanoacetate in the presence of ammonium hydroxide. In another embodiment of the invention, the ketone is cyclohexanone.

A reaction according to the present invention is substantially complete in less than 36 to 48 hours. In one embodiment of the invention, the reaction process is substantially completed in 24 to 36 hours. In a preferred embodiment, a reaction according to the present invention is substantially completed in less than 24 hours.

In one embodiment of the present invention, a molar ratio of ethylcyanoacetate:ketone is in the range of 1:0.5 to 4:2. In a preferred embodiment of the present invention, a molar ratio of ethylcyanoacetate:cyclohexanone is 2:1.

The organic solvent used in the Guareschi reaction can be an alcohol or another polar solvent. In a preferred embodiment the solvents are be methanol and ethanol. In addition, esters of cyanoacetate acid, such as for example, methylcyanoacetate can be used to replace ethylcyanoacetate in the Guareschi reaction.

The embodiments of the present invention are further described in the following example.

EXAMPLE 1

In a three-necked round flask equipped with a reflux condenser, a thermometer and an agitator 264.4 gm of ethylcyanoacetate and 312 gm of methanol are added. The solution is cooled to 8° C. while stirring. Two grams of ammonium acetate and 76.4 g or 1 equivalent versus 3 equivalents of ethylcyanoacetate are added at 8° C. 60 g of ammonium hydroxide solution 25% is added during 1 hour. During the addition of ammonium hydroxide, the temperature of the reaction mixture is maintained between 8 to 11° C. The solution is further maintained for half an hour at 8–11° C. The cooling is stopped and the temperature of the reaction mixture is allowed to rise during 45 minutes to 25° C. The suspension is maintained for 20 hours at 25° C. After 20 hours, the suspension is lightly heated and 50% sulfuric acid is added until the pH is 2. During the acidification the temperature is maintained in the range of 50–55° C. The reaction mass is cooled to 12° C. At 12° C. the suspension is mixed for half an hour and then filtered. The filter cake is washed with a mixture of methanol water (1:1 by weight). The mixture is then washed with water.

After drying, 163 gm of α,α',dicyano-β,β-pentamethyleneglutarimide (formula I) is obtained with an assay of 94% and a purity of 99.9%. This represents a yield of 85%.

What is claimed is:

1. A method of synthesizing pentamethylene glutarimides comprising:

reacting a ketone and ethylcyanoacetate under the reaction conditions of the Guareschi reaction in the presence of water and ammonium hydroxide for a time less than 36 to 48 hours.

2. The method according to claim 1, wherein the reaction conditions of the Guareschi reaction comprise a suitable temperature.

3. The method according to claim 1, wherein the ketone is cyclohexanone.

4. The method according to claim 1, wherein the suitable time is from 24 hours to 36 hours.

5. The method according to claim 1, wherein the suitable amount of time is less than 24 hours.

6. The method according to claim 1, wherein the molar ratio of ethylcyanoacetate to ketone is in the range of 1:2.

7. The method according to claim 1, wherein the reaction solvent is methanol or ethanol.

8. The method according to claim 2, wherein the temperature comprises an addition temperature and a reaction temperature.

9. The method according to claim 8, wherein the addition temperature is 8° C. to 10° C.

10. The method according to claim 8, wherein the reaction temperature is 25° C.

* * * * *